US006981979B2

(12) United States Patent
Nicolo

(10) Patent No.: US 6,981,979 B2
(45) Date of Patent: Jan. 3, 2006

(54) SURGICAL ANASTOMOTIC DEVICES

(76) Inventor: Enrico Nicolo, 515 Timber La., Jefferson Hills, PA (US) 15025

( * ) Notice: Subject to any disclaimer, the term of this patent is extended or adjusted under 35 U.S.C. 154(b) by 256 days.

(21) Appl. No.: 10/320,749

(22) Filed: Dec. 16, 2002

(65) Prior Publication Data
US 2003/0144675 A1 Jul. 31, 2003

Related U.S. Application Data

(60) Provisional application No. 60/340,451, filed on Dec. 14, 2001.

(51) Int. Cl.
A61B 17/04 (2006.01)
(52) U.S. Cl. ...................... 606/153; 128/898
(58) Field of Classification Search ............ 227/175.1; 606/153
See application file for complete search history.

(56) References Cited

U.S. PATENT DOCUMENTS

| 3,638,652 | A |   | 2/1972  | Kelley |
|-----------|---|---|---------|--------|
| 4,576,167 | A |   | 3/1986  | Noiles |
| 4,603,693 | A |   | 8/1986  | Conta et al. |
| 4,615,474 | A |   | 10/1986 | Strekopytov et al. |
| 4,817,847 | A |   | 4/1989  | Redtenbacher et al. |
| 5,005,749 | A |   | 4/1991  | Aranyi |
| 5,104,025 | A |   | 4/1992  | Main et al. |
| 5,119,983 | A |   | 6/1992  | Green et al. |
| 5,156,614 | A |   | 10/1992 | Green et al. |
| 5,170,925 | A |   | 12/1992 | Madden et al. |
| 5,172,845 | A |   | 12/1992 | Tejeiro |
| 5,180,092 | A |   | 1/1993  | Crainich |
| 5,188,274 | A |   | 2/1993  | Moeinzadeh et al. |
| 5,188,638 | A |   | 2/1993  | Tzakis |
| 5,197,648 | A |   | 3/1993  | Gingold |
| 5,197,649 | A |   | 3/1993  | Bessler et al. |
| 5,205,459 | A |   | 4/1993  | Brinkerhoff et al. |
| 5,217,472 | A |   | 6/1993  | Green et al. |
| 5,219,111 | A |   | 6/1993  | Bilotti et al. |
| 5,220,928 | A |   | 6/1993  | Oddsen et al. |
| 5,221,036 | A |   | 6/1993  | Takase |
| 5,242,457 | A |   | 9/1993  | Akopov et al. |
| 5,392,979 | A |   | 2/1995  | Green et al. |
| 5,411,508 | A |   | 5/1995  | Bessler et al. |
| 5,441,507 | A |   | 8/1995  | Wilk |
| 5,732,872 | A |   | 3/1998  | Bloduc et al. |
| 5,868,760 | A |   | 2/1999  | McGuckin, Jr. |
| 5,954,735 | A | * | 9/1999  | Rygaard ................ 606/153 |
| 5,993,468 | A | * | 11/1999 | Rygaard ................ 606/151 |
| 6,050,472 | A |   | 4/2000  | Shibata |
| 6,119,913 | A |   | 9/2000  | Adams et al. |
| 6,126,058 | A |   | 10/2000 | Adams et al. |
| 6,176,413 | B1|   | 1/2001  | Heck et al. |

* cited by examiner

Primary Examiner—Anhtuan T. Nguyen
Assistant Examiner—Bradford C. Pantuck
(74) Attorney, Agent, or Firm—Blynn L. Shideler; Krisanne Shideler; BLK Law Group

(57) ABSTRACT

Specifically, the anastomosis device of the present invention provides an anastomosis ring; such as but not limited to a ring of staples, in the form of an oval or ellipse. One specific embodiment of the present invention is a side to end anastomotic stapler with a row of staples formed in an elliptical pattern. Another embodiment of the present invention is a pair of anastomotic compression rings formed in an ellipse. A further embodiment of the invention is compression disc, rather than open ring structure.

18 Claims, 2 Drawing Sheets

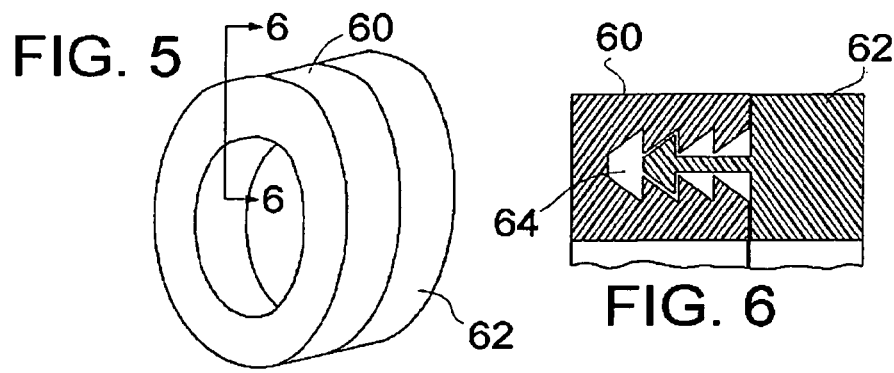
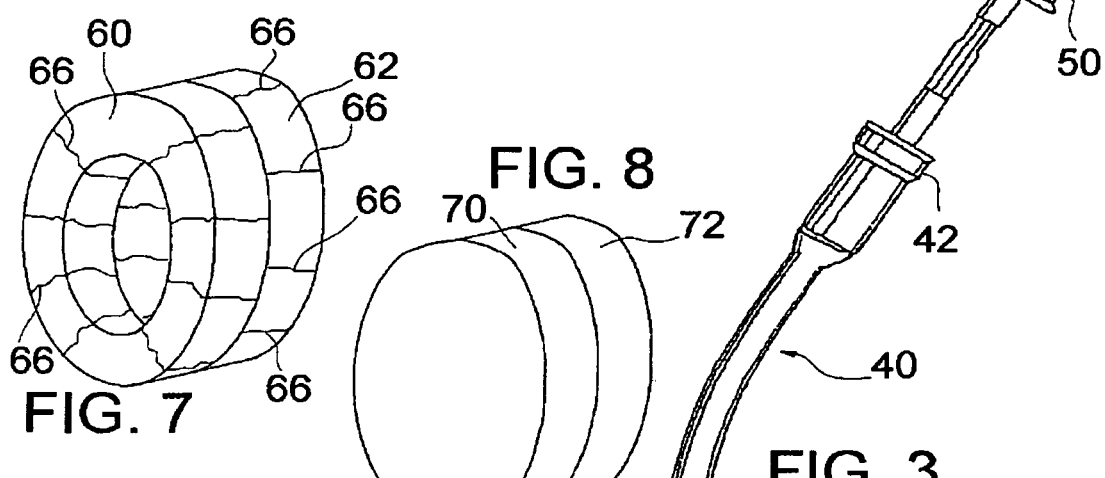
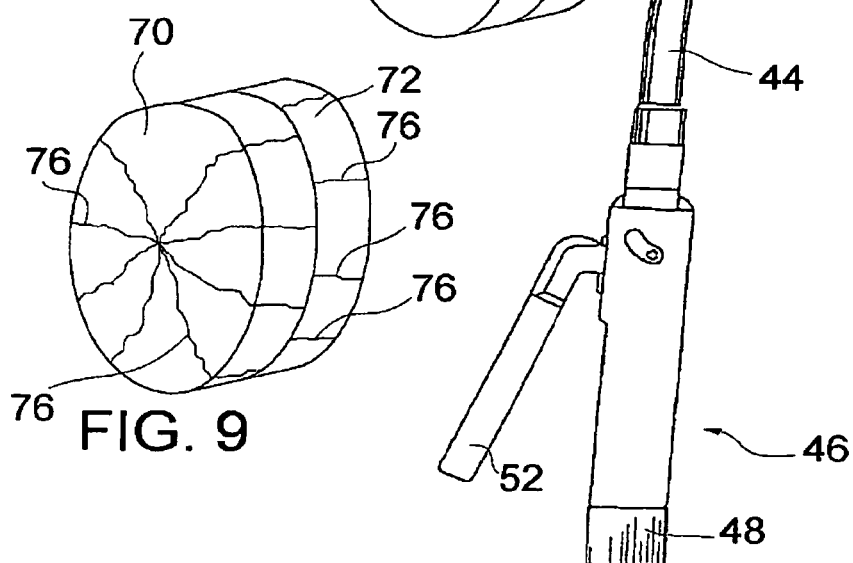

SURGICAL ANASTOMOTIC DEVICES

RELATED APPLICATION

This application claims the benefit of provisional application Ser. No. 60/340,451 filed Dec. 14, 2001 entitled "SURGICAL ANASTOMOTIC DEVICE" which is incorporated herein in its entirety.

BACKGROUND OF THE INVENTION

1. Field of the Invention

I, Enrico Nicolo, have developed improvements relating to the field of surgery and, particularly, my invention relates to a hollow viscus (intestine, vascular, urinary, etc.) resection and reconstruction device for hollow viscus surgery.

2. Background Information

Various types of surgical fastener applying instruments are known for the application of surgical fasteners to tissue. A common type of surgical fastener is a surgical staple. Surgical stapling instruments typically have a mechanism for firing a plurality of staples from a staple holding cartridge and an anvil disposed opposite the staple cartridge against which the staples are formed. Such instruments include, for example, linear staplers, which typically apply one or more parallel rows of staples, and circular staplers, which typically apply one or more concentric/circular rows of staples. In use, the surgeon will place tissue between the staple cartridge and anvil and, by firing the instrument, cause the staples to become clenched to the tissue.

Circular staplers are known and have been successfully used in surgical procedures for many years. Commercially available instruments include: the CEEA® circular stapler, manufactured by United States Surgical Corporation, Norwalk, Conn., and the ILS®. circular stapler manufactured by Ethicon, Inc., Blue Ash, Ohio. Various embodiments of circular staplers have been disclosed in U.S. Pat. Nos. 4,576,167; 4,603,693; 5,005,749; and 5,119,983. These instruments are typically indicated for use in gastric and esophageal surgery wherein tubular organs are joined to other anatomical structures.

The techniques of resecting a segment of the colon or intestines and an anastomosis of the cut ends are common procedures where a segment of diseased bowel must be removed for reasons such as inflammation, oncological process, obstructions, bleeding, perforation, trauma, etc. A conventional procedure for resection and anastomosis operates as follows. The first step is mobilization of a segment of the intestine to be resected. Mobilization is achieved by freeing the intestine from its cavity attachment and is then followed by separating its blood supply. The mobilization can be conducted laparoscopically or through opening the peritoneal cavity. Second, resection of the segment to be removed follows the mobilization procedure. Following the resection of the segment to be removed, the remaining ends of the bowel are anastomized to guarantee the continuity of the intestinal track. In an intestinal end-to-end anastomosis, a portion of the intestinal tract is removed (i.e., due to the presence of disease, such as cancer) as noted and the remaining ends are rejoined by using a circular stapler. To join the tubular structures, one end of the intestine is secured about an anvil and the other end of the intestine is held in place adjacent a staple cartridge. Preferably, the anvil has a shaft that is removably connected to the instrument. Once the anvil shaft is secured to the instrument, the anvil is drawn into close approximation to the stapling cartridge. The instrument is then fired to cause the staples to pass through tissue of both organs and become formed against the anvil. During the firing step, a circular knife is advanced to cut tissue inside the staple line, thereby establishing a passage between the organs. After firing, the instrument is typically removed by withdrawing the anvil through the staple line, after which the surgeon will carefully inspect the surgical site to ensure a proper anastomosis (joining) has been achieved.

In a further circular stapling example, U.S. Pat. No. 5,392,979 discloses a suturing apparatus which permits the anvil to be attached to, or detached from, the head with comparative ease, but in which the anvil is no longer detachable from the head if the distance between the two members has reached an optimal value for anastomosis. Then, a safety mechanism is released, whereupon it becomes possible to fire the staples. An indicator is used to provide a visual signal for the surgeon to know an optimal value of the head to anvil distance. A similar type of suturing apparatus is described in U.S. Pat. No. 5,205,459.

In addition to the above-described prior art, the following patents can be considered:

U.S. Patent Documents

| U.S. Pat. No. | Issue Date | Inventor | U.S. Classification |
|---|---|---|---|
| 3,638,652 | February, 1972 | Kelley | 227/179 |
| 4,615,474 | October, 1986 | Strekopytov et al. | 227/19 |
| 4,817,847 | April, 1989 | Redtenbacher et al. | 227/19 |
| 5,104,025 | April, 1992 | Main et al. | 227/19 |
| 5,197,648 | March, 1993 | Gingold | 227/19 |
| 5,411,508 | May, 1995 | Bessler et al. | 227/19 |
| 5,441,507 | August, 1995 | Wilk | 606/139 |
| 5,868,760 | February, 1999 | McGuckin, Jr. | 227/179 |
| 6,050,472 | April, 2000 | Shibata | 227/179 |
| 6,119,913 | September, 2000 | Adams et al. | 227/176 |
| 6,126,058 | October, 2000 | Adams et al. | 227/179 |

All of the prior art recognizes two types of existing staplers, namely, linear and circular. The identified prior art suggests that present stapling devices generally include GIA and EEA staplers which can be used to transect tissue in linear and circular fashions, respectively, with subsequent anastomosis with staples. The prior art suggests that the linear GIA is relatively versatile. The prior art further notes that the EEA is primarily suited for lower colonic circular anastomosis after a lesion has been surgically removed (via laparotomy or laparoscopically) or during a colostomy takedown procedure. Further examples of prior art can be found in U.S. Pat. Nos. 5,156,614; 5,170,925; 5,172,845; 5,180,092; 5,188,274; 5,188,638; 5,197,648; 5,197,649; 5,217,472; 5,219,111; 5,220,928; 5,221,036; and 5,242,457.

The present invention relates more particularly to the field of the circular staplers. The existing circular staplers do not match the shape of the hollow lumen, such as the colon. The colon, in the relaxed state, is essentially collapsed and even in the distended form does not form a circle. The anastomized lumen of the prior art is going to be a more unnatural circular state. The presence of scar tissue will hinder the ability of the anastomosis site from returning to the original shape of the lumen. The present invention attempts to address this problem.

SUMMARY OF THE INVENTION

The above problems with the prior art are addressed with an anastomosis device of the present invention. Specifically, the anastomosis device of the present invention provides an anastomosis ring, such as but not limited to a ring of staples, in the form of an oval or ellipse. One specific embodiment of the present invention is a side to end anastomotic stapler with a row of staples formed in an elliptical pattern. Another embodiment of the present invention is a pair of anastomotic compression rings formed in an ellipse. A further embodiment of the invention is compression disc, rather than open ring structure.

These and other advantages of the present invention will be clarified in the description of the preferred embodiments.

BRIEF DESCRIPTION OF THE DRAWINGS

FIG. 3 is a perspective view of another embodiment of a non-circular stapler for end to end anastomosis according to my invention;

FIG. 5 is a perspective view of an embodiment of non-circular compression rings for end to end or side to end or side to side anastomosis according to my invention;

FIG. 6 is a sectional view of the compression rings shown in FIG. 5;

FIG. 7 is a perspective view of an embodiment of frangible, non-circular compression rings for end to end or side to end or side to side anastomosis according to my invention;

FIG. 8 is a perspective view of an embodiment of non-circular compression discs for end to end or side to end or side to side anastomosis according to my invention; and FIG. 9 is a perspective view of an embodiment of frangible, non-circular compression discs for end to end or side to end or side to side anastomosis according to my invention.

DETAILED DESCRIPTION OF THE PREFERRED EMBODIMENTS

Elliptical Side to End Stapler

Figure 2:
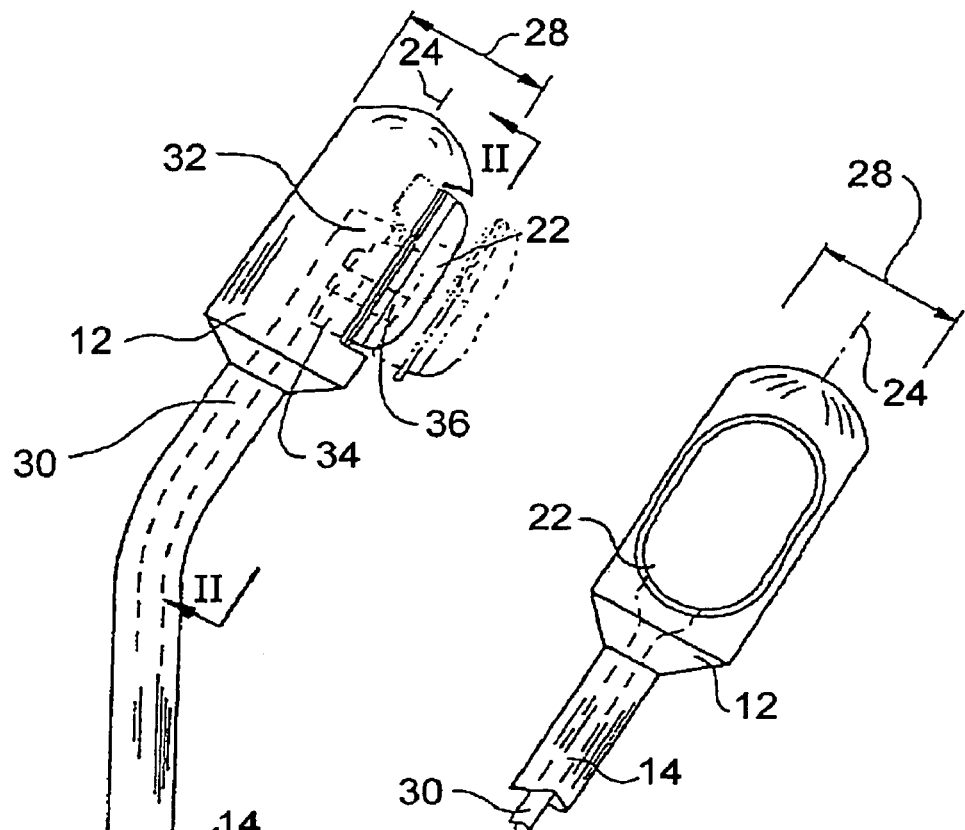
FIG. 2 is a front view of a head portion of the stapler illustrated in FIG. 1.
Figure 1:
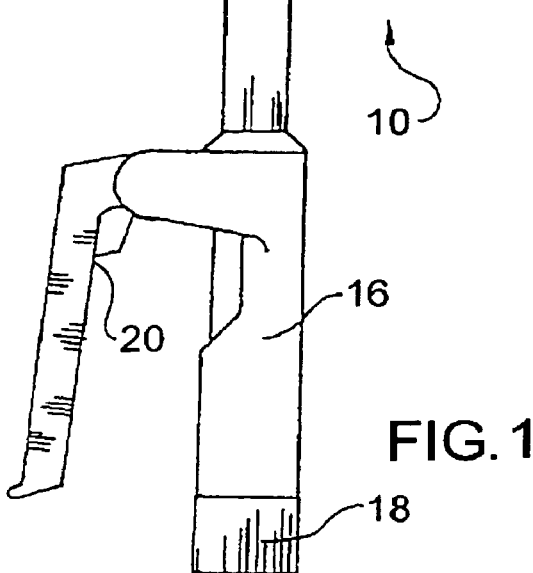
FIG. 1 is a perspective view of one embodiment of a non-circular stapler for side to end or side to side anastomosis according to my invention.

A surgical non-circular stapler 10 for side to end or side to side anastomosis according to my invention is illustrated in FIGS. 1 and 2. The stapler 10 of my invention is similar to existing end to end anastomotic staplers, commonly called "EEA staplers". The stapler 10 includes an actuating head portion 12 attached to an elongated hollow, tubular body 14 with a handle 16 on the opposed end of the body 14 from the head 12. The body 14 may include a bend, as shown in FIG. 1, to better conform to the shape of the patient's bowel. The handle 16 includes a rotary control 18 for actuating an anvil 22 of the stapler 10 in a conventional fashion, as will be described. The handle 16 also includes a trigger 20 for firing of the staples in a generally conventional manner, as will be described. The handle 16 may further include a conventional safety lock (not shown in detail) which acts to prevent firing of the staples until the anvil 22 is in the appropriate position relative to the head 12.

The construction of the head 12 differs significantly from existing EEA staplers. Unlike existing EEA staplers, the anvil 22 and an associated stapling mechanism (shown generally at 34) are positioned perpendicular to the longitudinal axis 24 of the head 12, as shown in FIG. 1. This construction allows the stapler 10 to perform side to end and side to side anastomosis. The end 26 of the head 12 is rounded to minimize potential trauma to the bowel. In constructing the head 12, it is important to minimize the widest dimension of the head 12 about the longitudinal axis 24. This dimension, shown at 28 in FIG. 1, will generally be along the axis of the anvil 22. The widest dimension 28 should be generally equal to the diameter of a circular head of conventional EEA staplers, which is generally about 30–35 mm. The widest dimension 28 is, therefore, less than about 35 mm for a conventional stapler 10 for application in the bowel. This dimension needs to be selected to allow the bowel, or other hollow viscus, to accept the head 12 of the stapler 10 without damage. The stapler 10 may be made of any size, as with conventional staplers, with the dimension 28 essentially the size of the stapler 10. Typical sizes would be 21, 25, 28 and 33 mm.

In addition to the dimensional considerations, the head 12 of my invention will require right angle drives for both the stapling mechanism 34 and operation of the anvil 22. The staples used in the head 12 are conventional staples positioned opposed from the anvil 22 in the conventional manner and are, therefore, not shown in detail. Additionally, the staples may further be fired together with an internal ring-shaped knife for trimming of the excess bowel portions, as conventional in the art. The staples and trimming knife of the stapling mechanism 34 do not form an essential part of the inventive concept of my invention and are, therefore, not shown in detail. FIG. 1 does schematically illustrate one type of right angle actuator for stapling mechanism 34 for firing of the staples (and for actuation of the trimming knife, if present). The right angle actuator includes a rod 30 extending along the inside of the tube 14 and movable along the tube by trigger 20 through a conventional linkage (not shown). The rod 30 includes a ramp 32 at the end thereof which will engage and actuate the stapling mechanism 34 which is shown schematically in FIG. 1. It will be apparent that many other right angle actuators are possible, with the present system being only a representative example.

The anvil 22 also requires a right angle drive. In operation, the anvil 22 can move relative to the head 12 by actuation of control 18. An open position of the anvil 22 relative to the head 12 is shown in phantom in FIG. 1. The operation of the anvil 22 is substantially the same as existing EEA staplers, except for the inclusion of a right angle drive. A stem 36 of anvil 22 will threadingly engage a rotatable sleeve (not shown) which is rotated by controller 18 through a rotatable shaft (not shown) extending through the tubular body 14. A pair of bevel gears may be provided within the head 12 between the rotatable sleeve and the rotatable shaft to accomplish the right angle drive. Bevel gears are well known for providing a right angle rotational drive. Other right angle rotational drives may be utilized, such as a flexible rotary shaft.

A stapler 10 for side to end and side to side anastomosis according to my invention operates as follows. The stapler 10 is inserted into the lower bowel segment to be attached. At the anastomosis site, the anvil 22 is advanced to the open position (shown in phantom in FIG. 1). The anastomosis sites of the two bowel segments to be attached are positioned between the anvil 22 and the head 12, and the anvil 22 is tightened by operation of the control 18 to clamp the relevant sections of the two bowel segments together. Known pull strings, and the like, may be used to assure the proper positioning of the bowel segments to be attached around stem 36. The trigger 20 is actuated to fire staples and the trimming knife, if any.

The anastomosis is now complete and the stapler 10 may be removed with any trimmed portions and pull string, or the like, secured between the anvil 22 and the head 12. The above operation is identical to existing EEA staplers except that the present invention allows for the side of the lower bowel segment to be attached to the end or to the side of the other bowel segment to be attached. Existing EEA staplers do not provide for this type of attachment between bowel segments.

This first embodiment of the present invention is a side to end elliptical, oval or generally non circular stapler 10. A similar side to end circular stapler is disclosed in my earlier patent U.S. Pat. No. 6,279,809 which is entitled: Circular Stapler For Side To End, Side To Side and End to Side Anastomosis which is incorporated herein by reference. This embodiment of the present invention is substantially identical to my earlier design except that the staples are aligned to form non-circular pattern, such as an oval or ellipse pattern, rather than the conventional circle. The shape of the oval or ellipse is not critical in the present invention, the purpose of the ellipse is to have the shape better approximate the shape of the lumen. The ellipse better approximates the lumen shape than does the prior art circle. Additionally the side to end configuration allows for a number of advantages. One advantage is a larger cross sectional area enclosed by the staples can be accommodated in the same width. Another advantage is the easier insertian and withdrawal of the tool into the patient. The width refers to the length across the area enclosed by the staples. In the circular stapler the width is the diameter of the circular pattern. In the present invention the width is across the narrower portion of the ellipse. The length of the ellipse along the axis of the stapler {i.e. the major axis of the ellipse} is not significant from a space or interference standpoint as shown in FIG. 2.

This invention can be considered as a unique combination of the GIA and the circular side to end stapler. The GIA provides for straight line stapling and the circular stapler is, of course limited to the circle pattern. The present invention allows for an elongated closed loop pattern that is particularly well adapted for the side to end stapler design of my earlier invention. This invention will have particular application in colon resection as well as gastric surgery.

Elliptical EEA Stapler

Figure 4:
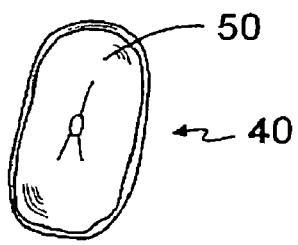
FIG. 4 is an end view of a head portion of the stapler illustrated in FIG. 3.

A second embodiment of the present invention is shown in FIGS. 3–4 and provides the elongated or elliptical shape of the first embodiment onto a conventional EEA stapler. The stapler 40 of my invention is similar to existing end to end anastomotic staplers, commonly called "EEA staplers". The stapler 40 includes an actuating head portion 42 attached to an elongated hollow, tubular body 44 with a handle 46 on the opposed end of the body 44 from the head 42. The body 44 may include a bend, as shown in FIG. 3, to better conform to the shape of the patient's bowel. The handle 46 includes a rotary control 48 for actuating an anvil 50 of the stapler 40 in a conventional fashion, as will be described. The handle 46 also includes a trigger 52 for firing of the staples in a generally conventional manner. The handle 46 may further include a conventional safety lock (not shown in detail) which acts to prevent firing of the staples until the anvil 50 is in the appropriate position relative to the head 42. This embodiment still allows the anastomosis site to better conform to the shape of the lumen. The end to end design is also particularly adapted for use in certain applications. A further advantage of this embodiment of the present invention is that the end to end construction is well known and accepted by practitioners.

Elliptical Open Compresion Rings

Staplers are not the only mechanical fasteners used for connecting tissue at an anastomosis site. Circular compression rings have been used in anastomotic procedures. The known compression rings are two ring members that clamp tightly together with the tissue to be anastomised therebetween. The rings hold the tissue tightly together, like staples, until the tissue heals. Currently these rings are made to be eventually absorbed by the body after healing, again similar to the staples often used in anastomotic procedures. These known circular rings suffer the same disadvantages as the circular staplers discussed above.

This embodiment of the present invention shown in FIGS. 5–6 provides forming the compression ring members 60 and 62 with an elongated or ellipse or oval shape. The elongated shape of the compression ring members 60 and 62 will provide the same advantages as discussed above for the elliptical array or staples in the circular staplers 10 and 40. The elongated shape must be accounted for in the attachment mechanism 64, shown in FIG. 6, utilized between the ring members 60 and 62. Latching clamps or other locking mechanism allowing linear motion of the respective clamping ring members 60 and 62 can be used. Other than the shape of the ring members, together with an attaching member 64 that accommodates the non-circular shape of the ring members 62 and 60, the remaining aspects of this embodiment of the present invention may be conventional.

In addition to the advantages to the anastomosis site provided by the shape of the individual rings 60 and 62, the shape of the rings 60 and 62 will allow them to be more easily passed through the healed lumen due to the elongated shape. This allows for the compression rings 60 and 62 to be made of a material that is not bio-absorbable, if desired. This option may allow a greater compression force to be created between the ring members 60 and 62, or a decrease in the material needed to form the ring members 60 and 62 due to a greater variety of suitable materials for forming the ring members 60 and 62. If formed of a non-bio-absorbable material it is obvious that any compression ring would need to either stay permanently at the anastomotic site or pass through the anastomised lumen following healing. The holding of the compression ring at the anastomotic site permanently is generally not desired and may need additional elements to integrate the ring into the healed lumen. With the current ring member configurations the ring would be expected to naturally separate from the healed lumen. The elongated shape of the compression ring members of the present invention allow the ring to be more easily passed through the healed lumen. It is expected that the elongated open compression ring members of the present invention will be placed into a lumen for the anastomosis. After the lumen is healed the ring, if formed of a non-bio-absorbable material will naturally separate from the healed lumen and simply pass through the lumen.

Frangible Open Compression Rings

A further embodiment of the present invention builds on the elliptical open compression ring of the present invention discussed above. This feature of the present invention is shown in FIG. 7 and is to form each of the ring members 60 and 62 as a frangible component that will effectively disintegrate into smaller components when the anastomosis site has healed and the ring separates from the anastomotic site to pass through the lumen. This embodiment only relates to the ring members formed, at least in part, by non-bio-absorbable material. The object may be accomplished by forming connecting ring member segments or break lines 66 of biodegradable material connecting adjacent individual sections of the ring member formed of the non-bio-absorbable material. Alternatively the non-absorbable ring member sections may be connected to each other with a weakened portion of the ring member (e.g. a groove or slot or minimum member thickness therebetween). In this construction the separation of the ring from the anastomotic site will result in the disintegration of the ring members into the individual sections.

The key advantage of this embodiment is that the individual sections of each individual ring member will separate following the healing of the anastomotic site thereby easing the passing of the rings through the lumen. This embodiment is usable with the elongated ring members of the present invention. Additionally this aspect of the present invention can be utilized with circular ring member shapes of the prior art, except that these no longer need to be formed completely of bio-absorbable material.

Compression Discs

Another aspect of the present invention is the use of closed compression rings 70 and 72, which may also be called compression discs 70 and 72 shown in FIGS. 9 and 10. The compression discs 70 and 72 of this embodiment of the present invention may be formed as discussed above including the elongation of the individual disc members 70 and 72. The compression disc of the present invention may be preferred to be shaped in the elongated fashion for the advantages provided to the lumen and for ease of operation, but is not limited thereto. A circular disc shape may also be used. The only difference of the disc and ring of the present invention is that the individual disc members are solid rather than ring shaped members (i.e. no opening through the center). This feature is to prevent the anastomised lumen from being used by the body until the compression discs 70 and 72 has been removed. As with the compression ring above the compression disc may be removed naturally through bio-absorption or passing through the healed lumen.

This aspect of the present invention will have application where the lumen is not to be used until after healing. One particular example is in the use of temporary collostomy procedures that are currently used (also called two-stage Hartman operations). Currently when the temporary collostomy procedure is to be removed the currently unattached lower bowel portion is attached in the second stage of the operation. The present invention allows this to be attached to the upper bowel portion at the inception of the temporary collostomy in an end to side attachment (as will be understood by those of ordinary skill in the art). The closed discs will prevent the lower bowel portion from being used by the body until after the site has healed. The only step left for removing the temporary collostomy when using the compression discs 70 and 72 of the present invention is to separate and close the remaining portion of the upper bowel (i.e. the portion forming the collostomy) in a conventional fashion, preferably relatively close to the now healed anastomotic site formed by the compression disc (e.g. immediately downstream). This should significantly decrease the time needed for the second stage. Further the body itself will give an indication of when the second stage is proper, which is after the compression ring site has healed and the body can again use the lower bowel.

Frangible Compression Discs

Another aspect of the present invention is shown in FIG. 9 and is to form the compression discs 70 and 72 of the present invention as frangible non-bio-absorbable components, at least in part. This aspect of the present invention is intended to provide ease of passage through the healed lumen for the disc components 70 and 72. This embodiment may be formed essentially the same as the frangible compression rings discussed above including break points 76. As with the compression disc discussed above, the frangible compression disc of the present invention may be preferred to be shaped in the elongated fashion for the advantages provided to the lumen and for ease of operation, but is not limited thereto. A circular disc shape may also be used. The frangible disc construction may allow for a circular compression disc shape to more easily be accommodated.

Closed Interior Staplers

Another aspect of the present invention is to form the closed interior anastomosis, such as formed with the compression discs of the present invention, with staplers. This can be done with conventional staplers including EEAs or my prior side to end device if the interior knife is removed. This will be easily understood by those of ordinary skill in the art.

The invention has been described with reference to the preferred embodiment. Obvious modifications and alterations will occur to others upon reading and understanding the proceeding detailed description. It is intended that the invention be construed as including all such modifications and alterations.

I claim:

1. A surgical resection and reconstruction method for a tubular body lumen comprising the steps of:
    Providing a surgical anastomotic apparatus having an elongate tubular body and elements forming a closed loop anastomotic ring in the reconstructed hollow lumen and in a general anastomosis plane for reconstruction of the body lumen, wherein the anastomotic ring is non-circular, and wherein the elements of the surgical anastomotic apparatus have a dimension greater in one direction within the anastomosis plane than in an orthogonal direction in the anastomosis plane, whereby the greater dimension defines a long axis for the elements of the surgical anastomotic apparatus; and
    At least one of inserting and withdrawing the elongate tubular body and ring through the interior of the body lumen and longitudinally along an interior portion of the body lumen with the long axis of the elements of the surgical anastomotic apparatus generally parallel with the axis of the tubular body lumen.

2. The method of claim 1 wherein the anastomotic ring is one of an oval and an ellipse.

3. The method of claim 2 wherein the surgical anastomotic apparatus is a surgical stapler and the method includes both inserting and withdrawing the surgical stapler through the body lumen with the long axis of the elements of the surgical stapler generally parallel with the axis of the tubular body lumen.

4. The method of claim 2 wherein the surgical anastomotic apparatus is a pair of open center compression rings.

5. The method of claim 4 wherein the pair of open center compression rings are withdrawn through the body lumen with the long axis of the rings generally parallel with the axis of the tubular body lumen.

6. The method of claim 2 wherein the surgical anastomotic apparatus is a pair of closed center compression discs.

7. The method of claim 6 wherein the pair of closed center compression discs are withdrawn through the body lumen with the long axis of the discs generally parallel with the axis of the tubular body lumen.

8. The method of claim 6 wherein the discs are frangible and further including the step of having the discs disintegrate into smaller components when the anastomosis site has healed.

9. The method of claim 1 wherein the surgical anastomotic apparatus is a surgical stapler, wherein the elements forming a closed loop anastomotic ring are a stapler anvil and stapler head, and the method includes both inserting and withdrawing the surgical stapler through the body lumen with the long axis of the anvil and head of the surgical stapler generally parallel with the axis of the tubular body lumen.

10. The method of claim 1 wherein the surgical anastomotic apparatus is a pair of open center compression rings.

11. The method of claim 10 wherein the pair of open center compression rings are substantially elliptical and are withdrawn through the body lumen with the long axis of the rings generally parallel with the axis of the tubular body lumen.

12. The method of claim 10 wherein the rings are substantially elliptical and are frangible and further including the step of having the rings disintegrate into smaller components when the anastomosis site has healed.

13. The method of claim 1 further including forming the closed loop anastomotic ring with staples without the step of trimming the tissue of the lumen within the anastomotic ring with the anastomotic device.

14. The method of claim 13, wherein the anastomosis site is at the side of at least one lumen portion wherein the closed loop anastomotic ring will have an interior closed by the untrimmed tissue of the side of the lumen while the anastomotic site is healing, and wherein the untrimmed tissue of the side of the lumen is not present after the anastomotic site is healed.

15. A surgical resection and reconstruction method for a tubular body lumen comprising the steps of:

Providing a surgical anastomotic apparatus having elements forming a closed loop anastomotic ring in the reconstructed hollow lumen and in a general anastomosis plane for reconstruction of the body lumen, wherein the anastomotic ring is non-circular, and wherein the elements of the surgical anastomotic apparatus have a dimension greater in one direction within the anastomosis plane than in an orthogonal direction in the anastomosis plane, whereby the greater dimension defines a long axis for the elements of the surgical anastomotic apparatus, wherein the surgical anastomotic apparatus is a pair of open center compression rings and wherein the rings are frangible;

At least one of inserting and withdrawing the surgical anastomotic apparatus through the body lumen with the long axis of the elements of the surgical anastomotic apparatus generally parallel with the axis of the tubular body lumen; and further including the step of having the rings disintegrate into smaller components when the anastomosis site has healed.

16. A surgical resection and reconstruction method for a tubular body lumen comprising the steps of:

Providing a surgical anastomotic apparatus having elements forming a closed loop anastomotic ring in the reconstructed hollow lumen and in a general anastomosis plane for reconstruction of the body lumen, wherein the anastomotic ring is non-circular, and wherein the elements of the surgical anastomotic apparatus have a dimension greater in one direction within the anastomosis plane than in an orthogonal direction in the anastomosis plane, whereby the greater dimension defines a long axis for the elements of the surgical anastomotic apparatus, and wherein the surgical anastomotic apparatus is a pair of closed center compression discs; and At least one of inserting and withdrawing the surgical anastomotic apparatus through the body lumen with the long axis of the elements of the surgical anastomotic apparatus generally parallel with the axis of the tubular body lumen.

17. The method of claim 16 wherein the pair of closed center compression discs are substantially elliptical and are withdrawn through the body lumen with the long axis of the discs generally parallel with the axis of the tubular body lumen.

18. The method of claim 16 wherein the discs are substantially elliptical and are frangible and further including the step of having the discs disintegrate into smaller components when the anastomosis site has healed.

* * * * *